(12) United States Patent
Abedin et al.

(10) Patent No.: US 11,194,852 B2
(45) Date of Patent: Dec. 7, 2021

(54) RAPID CROSS-VALIDATED GROUND TRUTH ANNOTATION OF LARGE IMAGE DATASETS FOR IMAGE ANALYTICS

(71) Applicant: INTERNATIONAL BUSINESS MACHINES CORPORATION, Armonk, NY (US)

(72) Inventors: Shafiqul Abedin, San Jose, CA (US); David Beymer, San Jose, CA (US); Hakan Bulu, San Jose, CA (US); Yaniv Gur, San Jose, CA (US); Mehdi Moradi, San Jose, CA (US); Anup Pillai, San Jose, CA (US); Tanveer Syeda-Mahmood, San Jose, CA (US); Guy Talmor, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 496 days.

(21) Appl. No.: 15/654,488

(22) Filed: Jul. 19, 2017

(65) Prior Publication Data

US 2019/0026278 A1 Jan. 24, 2019

(51) Int. Cl.
*G06F 16/00* (2019.01)
*G06F 16/432* (2019.01)
(Continued)

(52) U.S. Cl.
CPC ...... *G06F 16/434* (2019.01); *G06F 16/24573* (2019.01); *G06F 16/436* (2019.01); *G06F 16/55* (2019.01); *G06F 40/169* (2020.01); *G06F 40/186* (2020.01); *G16H 30/20* (2018.01); *G16H 30/40* (2018.01); *G16H 40/67* (2018.01); *G06T 2207/30004* (2013.01); *G16H 10/60* (2018.01)

(58) Field of Classification Search
CPC .. G06F 16/434; G06F 16/24573; G06F 16/55; G06F 16/436; G06F 17/241; G06F 17/248; G06F 17/30398; G06F 17/30306; G06F 17/30967; G06F 17/30392; G06F 17/30421; G06F 40/186; G06F 40/169; G06T 2207/30004; G06T 7/0012; G06T 19/00; G06T 2210/41; G06T 2207/30012; G06T 2219/004; G06T 17/20; G06T 17/00; G06T 15/10; G06T 15/00; G16H 40/67; G16H 30/20; G16H 30/40; G16H 10/60
USPC .......................................... 707/779; 345/419
See application file for complete search history.

(56) References Cited

U.S. PATENT DOCUMENTS 9,262,587 B2 2/2016 Barr et al.
2007/0052734 A1 3/2007 Skinner, Jr. et al.
(Continued)

*Primary Examiner* — Ashish Thomas
*Assistant Examiner* — Suman Rajaputra
(74) *Attorney, Agent, or Firm* — Erik Huestis; Stephen Kenny; Foley Hoag, LLP

(57) ABSTRACT

Annotation of large image datasets is provided. In various embodiments, a plurality of medical images is received. At least one collection is formed containing a subset of the plurality of medical images. One or more image from the at least one collection is provided to each of a plurality of remote users. An annotation template is provided to each of the plurality of remote users. Annotations for the one or more image are received from each of the plurality of remote users. The annotations and the plurality of medical images are stored together.

17 Claims, 7 Drawing Sheets

(51) Int. Cl.
 G06F 16/435 (2019.01)
 G06F 16/2457 (2019.01)
 G06F 16/55 (2019.01)
 G16H 40/67 (2018.01)
 G16H 30/40 (2018.01)
 G16H 30/20 (2018.01)
 G06F 40/169 (2020.01)
 G06F 40/186 (2020.01)
 *G16H 10/60* (2018.01)

(56) References Cited

U.S. PATENT DOCUMENTS

| | | | |
|---|---|---|---|
| 2012/0130223 A1* | 5/2012 | Reicher | G06T 11/60 600/407 |
| 2015/0052058 A1* | 2/2015 | McCown | G06Q 10/063114 705/51 |
| 2015/0278443 A1* | 10/2015 | Bogaert | G06F 19/321 705/3 |
| 2016/0103816 A1 | 4/2016 | Grady et al. | |
| 2016/0253456 A1 | 9/2016 | Goede | |
| 2016/0350484 A1* | 12/2016 | Son | G16H 30/20 |
| 2018/0021022 A1* | 1/2018 | Lundberg | A61B 8/0841 600/424 |
| 2018/0137244 A1* | 5/2018 | Sorenson | G16H 50/20 |
| 2018/0341747 A1* | 11/2018 | Bernard | G06F 40/30 |
| 2018/0344292 A1* | 12/2018 | Viggen | A61B 8/06 |
| 2018/0349554 A1* | 12/2018 | Jackson | G16H 30/20 |
| 2019/0038356 A1* | 2/2019 | Schmitt | A61B 6/461 |

* cited by examiner

RAPID CROSS-VALIDATED GROUND TRUTH ANNOTATION OF LARGE IMAGE DATASETS FOR IMAGE ANALYTICS

BACKGROUND

Embodiments of the present invention relate to annotation of large image datasets, and more specifically, to rapid cross-validated ground truth annotation of large image datasets for image analytics.

BRIEF SUMMARY

According to embodiments of the present disclosure, methods of and computer program products for annotation of large image datasets are provided. A plurality of medical images is received. At least one collection is formed containing a subset of the plurality of medical images. One or more image from the at least one collection is provided to each of a plurality of remote users. An annotation template is provided to each of the plurality of remote users. Annotations for the one or more image are received from each of the plurality of remote users. The annotations and the plurality of medical images are stored together.

DETAILED DESCRIPTION

Figure 1:
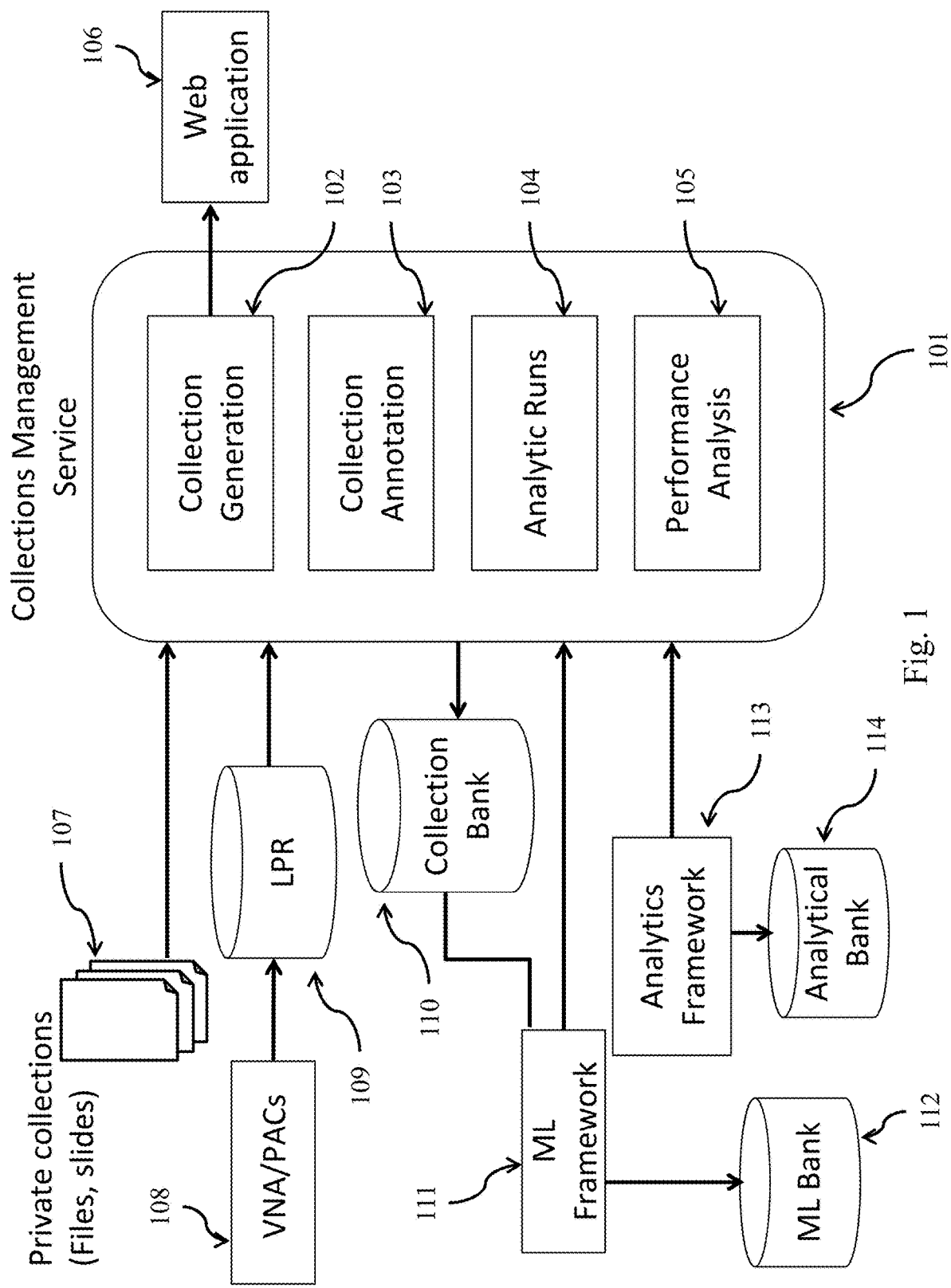
FIG. 1 illustrates an exemplary architecture for a system for annotation of large image datasets according to embodiments of the present disclosure.

One of the critical challenges facing the development of scalable decision support systems based on machine learning on big data is the availability of labeled datasets. Specifically, deep learning is increasingly being recognized as a scalable way to address clinical decision support in healthcare. However, it needs a very large number of labeled examples as well. Obtaining a large amount of labeled data is difficult both due to the lack of availability of a large number of clinical experts and the inherent complexity of labeling large 3D and 4D study volumes in CT and MM using desktop tools. Even though large numbers of imaging studies are available from hospital PACS systems, only a small number of imaging studies are stored with annotations at the regional level with the findings mostly described verbally in reports. Unlike human operators, a machine interpreting a whole imaging study needs the annotation of many more features within images, such as imaging modes, viewpoints from which imaging is taken, or volumetric segmentation of anatomical structures for training machine recognizers. Creating annotated collections of millions of images is a very large scale effort requiring the availability of a large number of clinical experts. Complicating this further is the lack of consensus found in annotations among experts.

To provide robust annotation of large image datasets, various systems according to the present disclosure are not limited with respect to data types, can operate via a web application, and provide significant ease of use. In addition, cross-validation and annotation status tracking are provided with respect to the users of the collection. Accordingly, the present disclosure enables labeling images for disease occurrences in a web-based semi-automatic fashion to ease the labeling burden of clinical experts and to scale to large collections.

According to various embodiment of the present disclosure, a platform is provided for creation and organization of image collections from large image repositories for the purpose of training and testing image analytics algorithms and products. Collections are assigned to registered clinical experts for annotation. These annotations serve as ground truth for training and testing of analytics. Various browser-based tools are provided for annotation of medical images, and various data structures are provided that support search and retrieval of collections and annotations. The running of analytics on collections and the generation of performance reports may be organized through the same user interface.

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

With reference now to FIG. 1, an exemplary system architecture 100 according to embodiments of the present disclosure is illustrated. A Collections Management service 101 provides a variety of services 102 . . . 105. Collections Management service 101 is accessible via web application 106.

In various embodiments, Collections Management service 101 provides collection generation 102 of medical data collections. In various embodiments, Collections Management service 101 provides collection annotation 103 of medical data such as imagery in the various collections under management. In various embodiments, Collections Management service 101 provides analytic runs 104 against the medical data such as imagery in the various collections under management. Based up on the output of analytic runs 104, Collections Management service 101 provides performance analysis of the various analytics.

A variety of data stores 107 . . . 114 may provide medical data to or receive data from service 101. In various embodiments, private collections 107, such as slides, electronic files, or paper files are provided to Collections Management service 101. In various embodiments, a Vendor Neutral Archive (VNA) and/or picture archiving and communication system (PACS) 108 containing images and documents provide data to Collections Management service 101. In some embodiments, images and document from the VAN and/or PACS populate a Longitudinal Patient Record (LPR) 109, from which Collections Management service 101 retrieves the data.

Once collections of underlying medical data are formed through collection generation 102, information regarding those collections may be stored in collection bank 110. Various machine learning (ML) algorithms may be applied to the stored collection via machine learning framework 111. Various machine learning algorithms may be stored and retrieved from ML bank 112 for application to the medical data. Likewise, analytics framework 113 may perform various analytics processes on the collections and deliver the results to Collections Management service 101. Analytics processes may be retrieved from analytics bank 114 for application to the medical data.

The present disclosure provides common platform to organize collections, organize annotation of collections, organize running of analytics on collections, organize testing and benchmarking efforts and enable continuous improvement of algorithms for productization. In various embodiments, this is provided as a hosted service.

In various embodiments, collections are created from various sources. For example, unstructured connections may include a group of files in a directory, or an imaging file list pointing to raw image files. Such unstructured collections, lists thereof, or individual slides containing data may be uploaded to a data store and indexed in the LPR. Similarly, collections may be generated from batch draws from a VNA or PACS, and then automatically ingested into LPR. Custom collections may also be created through the search and browse features described below.

In various embodiments, collections may be browsed through a user interface. In some embodiments, a hierarchical view of the collections is provided. In addition, in some embodiments, collections may be searched according to user-defined criteria. Images belonging to a collection may likewise be searched. Search results may be combined to form a new collection. For example, while data may originally be ingested from PACS organized by patient and study, a custom collection may be defined of all images from a certain study type having a given label (e.g., all echocardiograms labeled for stenosis). In some embodiments, the images resulting from a search are displayed to a user to be marked for inclusion in a collection.

Collections may be further managed by a user, updating their contents, attaching metadata such as descriptions, or attaching additional features. Once a collection is organized, the images contained therein are stored in LPR. Future retrievals may be drawn from LPR instead of from an underlying PACS.

Figure 2:
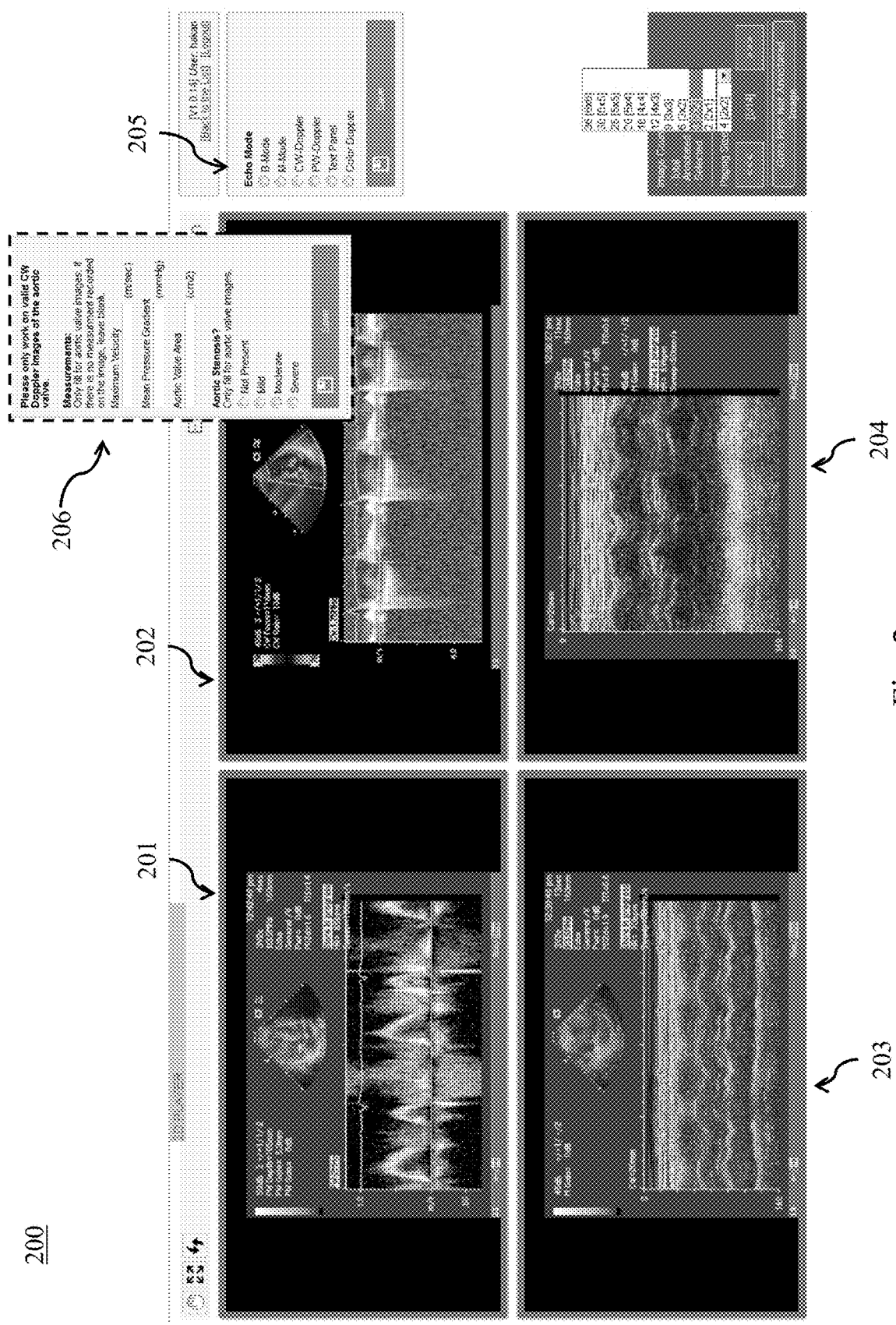
FIG. 2 illustrates an exemplary user interface for annotation of large image datasets according to various embodiments of the present disclosure.

Referring to FIG. 2, a user interface 200 for annotation of large image datasets is illustrated. According to various embodiments, a collection for annotation is retrieved by searching or browsing. A plurality of images 201 . . . 204 from a subject collection are displayed. Labels for each image may be selected through label selection pane 205, which in this example prompts a user to indicate an echo mode for the subject image. Second exemplary selection pane 206 (inset) prompts a user to determine various measurements from a CW Doppler image, and label for stenosis.

In various embodiments, creation of slide level annotation is provided. Upon annotation, an index entry in LPR may be created. Such slides may then included implicitly in additional collections.

In various embodiments, regional annotation is provided. A single study is displayed for annotation. An annotation template appropriate to the individual study is displayed. In some embodiments, 3D interpolation across study frames is provided to increase the ease of annotation of contours. Annotations may be stored along with the corresponding study back in LPR as features.

As noted above, the present disclosure enables running of analytics on collection within the provided framework. The analytics framework allows registration of analytics for later use and storage in the analytics bank. Individual analytics processes may be launched through specification of collections to run. At that time, the analytics description is loaded from the analytics bank. A collection is selected on which to run the analytics. The analytics are run on the collection. Performance results are reported.

In some embodiments, the analytics are ported to different platforms through the analytics framework. In this way, translation to different platforms is enabled for the runs.

According to various embodiments, testing and benchmarking is provided. A variety of evaluation criteria are provided for different types of algorithms. For example, dice coefficients, sensitivity/specificity, accuracy, and F-number may be computed. These algorithm performance numbers can be generate for each analytics run, by invoking evaluation algorithms after the results are recorded. This enables separation of the evaluation from algorithm development. The performance of algorithms in terms of speed, memory, I/O and other metrics is recorded for comparison and analysis.

In various embodiments, systems according to the present disclosure may be offered as a hosted service, such as in the cloud. Clinicians may be enrolled for annotation tasks. In addition, other experts may be enrolled for annotation for tasks where clinicians are not needed. In some embodiments, a payment process is provided. In such embodiments, the number of annotations done by each expert is recorded, and compensation is provided through a payment system at a rate reflecting the total annotations performed.

Figure 3:
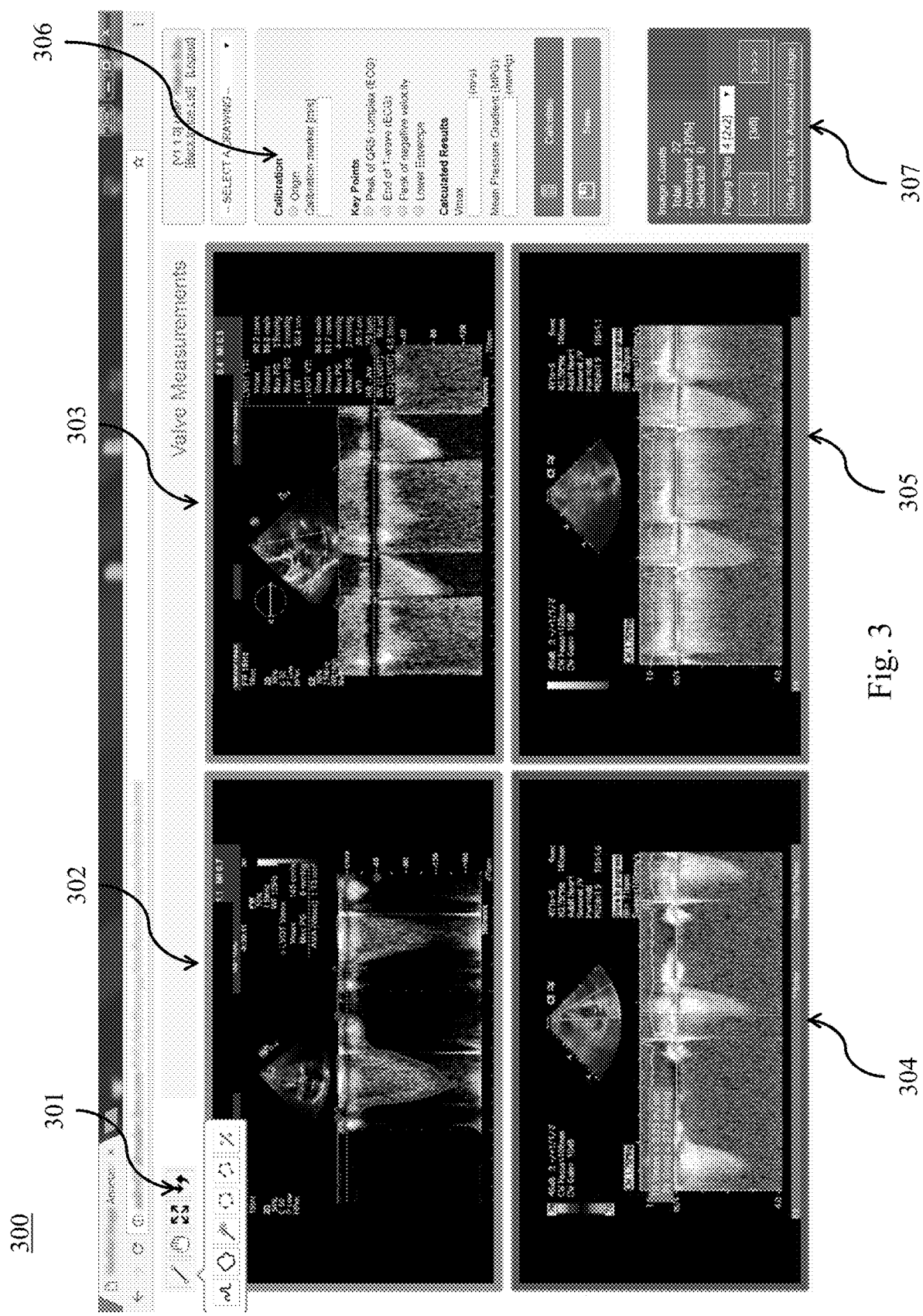
FIG. 3 illustrates an exemplary user interface for annotation of large image datasets according to various embodiments of the present disclosure.

Referring to FIG. 3, another exemplary user interface 300 for annotation of large image datasets is illustrated. In various embodiments, this user interface is displayed to a user after login, and may be accessed via a navigation system such as a task desktop. Toolbar 301 provides drawing tools including, for example, zooming and panning abilities. Frames around images 302, 303 indicate the annotated images. The frame around image 304 indicates the selected image. The frame around image 305 indicates the image that has not been annotated yet. In various embodiments, the frames around images 302 . . . 305 are color-coded. Annotation template 306 is used to set and save the annotation values and is supported by a task-specific template-generating pipeline. Statistical frame 307 gives some key information to the user about status of the annotation task. For example, in some embodiments frame 307 provides the number of total and annotated image counts and allows the user to navigate through the entire collection, or change the arrangement/number of images on page.

According to various embodiments, systems are provided for labeling and annotation of medical images on the web. Such systems allow the efficient use of limited resources through expert sourcing. In addition, they solve data and user management issues, allowing multiple annotators for a project, multiple annotations per image, and the ability to index and search across collections and annotations. System according to the present disclosure provide the tooling for different annotation tasks, from image level labeling to object contouring. Advantages of various embodiments include: flexibility of user interface in adding new features; scalability across image, tasks, users and tools dimensions; search capabilities across all labels, users, and task templates through indexing. Various embodiments provide extensive support for data and user management that allows for streamlined use of data in machine learning algorithms, such as the active learning/self-training process described in the previous section.

Platforms according to the present disclosure include a user interface such as those described above, supported by backend modules including user management, collections management, and annotations management.

In various embodiments, a user management module provides tools to register users in a database and control access to specific images and collections. Information about the annotators' expertise is also registered to allow for algorithmic matching of annotators to tasks.

In various embodiments, a collections management module models collections as a set of images with their metadata, along with a task and list of annotators. In various embodiments, the data model for a collection can handle multiple annotators across tasks, multiple annotations for the same attribute by different annotators for cross-validation, as well as one image as part of many collections. Collections may index the web address of anonymized images that are served through a secure HIPPA-compliant server. Collections and the annotations may also be indexed in a database that allows search and retrieval across different image and label attributes such as mode, modality/specialty, and annotated clinical features.

In various embodiments, an annotations management module supports the operations of defining annotation tasks, assigning annotators to collections based on their expertise, and tracking work progress by providing annotation completeness reports. The task and assignments per collection may also be stored in the collections database. The process of task and collection assignment to annotators may be performed by authorized administrators, who have access to the image archive and the user database. User interfaces are provided to support these operations.

The flexibility of task building is obtained in various embodiments through a toolkit that allows a user to build a template. The template defines the type of task (such as contouring, labeling, or measurement recording) and also the tools needed for performing the task. The user interface automatically interprets the template and shows the right tools and forms with the assigned collection of images. An example of such a resulting interface is described above with reference to FIG. 3. In this example, users are expected to mark a keypoint and draw a number of contours.

Figure 4:
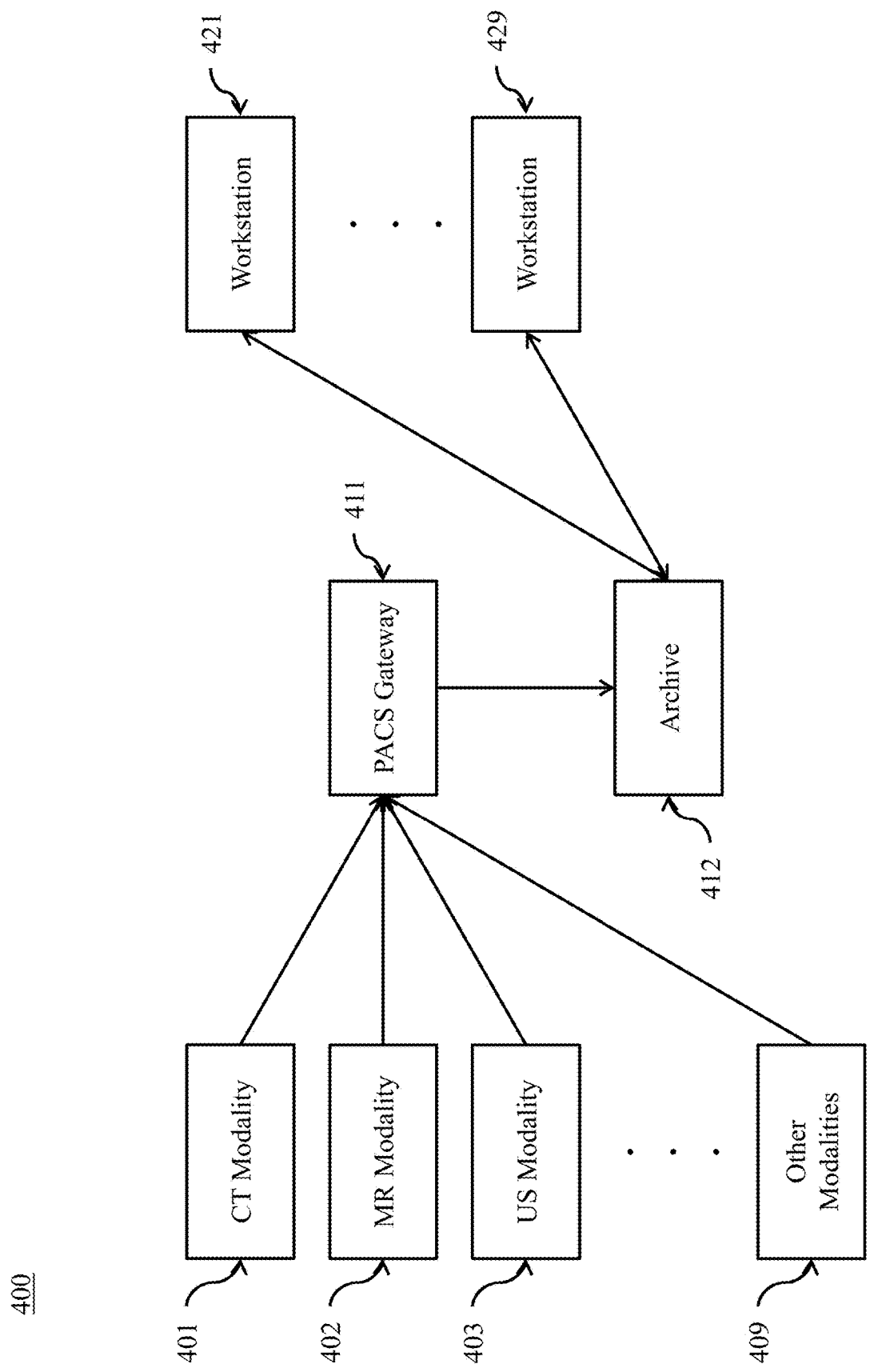
FIG. 4 depicts an exemplary Picture Archiving and Communication System.

Referring to FIG. 4, an exemplary PACS 400 consists of four major components. Various imaging modalities 401 . . . 409 such as computed tomography (CT) 401, magnetic resonance imaging (MM) 402, or ultrasound (US) 403 provide imagery to the system. In some implementations, imagery is transmitted to a PACS Gateway 411, before being stored in archive 412. Archive 412 provides for the storage and retrieval of images and reports. Workstations 421 . . . 429 provide for interpreting and reviewing images in archive 412. In some embodiments, a secured network is used for the transmission of patient information between the components of the system. In some embodiments, workstations 421 . . . 429 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 411 comprises a quality assurance (QA) workstation. The QA workstation provides a checkpoint to make sure patient demographics are correct as well as other important attributes of a study. If the study information is correct the images are passed to the archive 412 for storage. The central storage device, archive 412, stores images and in some implementations, reports, measurements and other information that resides with the images.

Once images are stored to archive 412, they may be accessed from reading workstations 421 . . . 429. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 421 . . . 429 to burn patient studies for distribution to patients or referring physicians.

In some implementations, a PACS includes web-based interfaces for workstations 421 . . . 429. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 5:
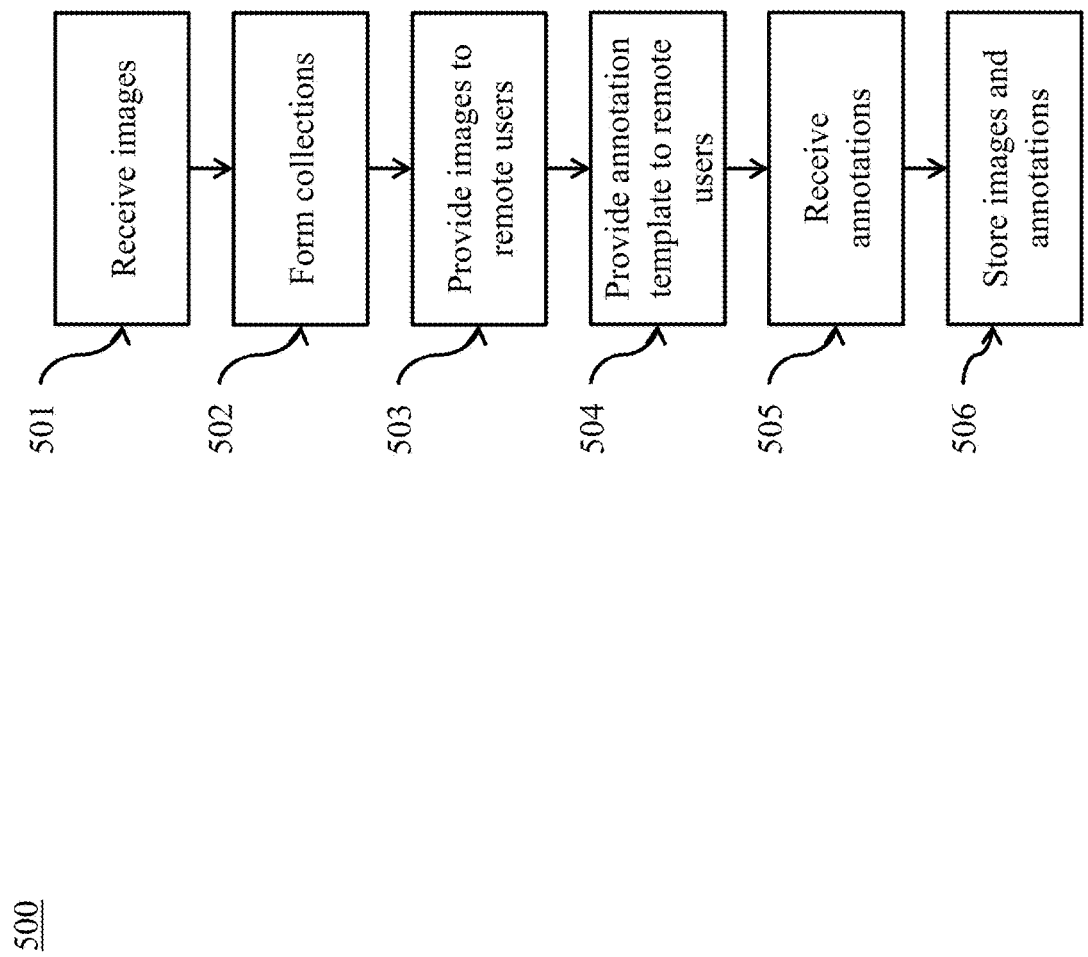
FIG. 5 illustrates a method of annotation of large image datasets according to various embodiments of the present disclosure.

Referring to FIG. 5, a method of annotation of large image datasets is illustrated according to embodiments of the present disclosure. At 501, a plurality of medical images is received. At 502, at least one collection is formed containing a subset of the plurality of medical images. At 503, one or more image from the at least one collection is provided to each of a plurality of remote users. At 504, an annotation template is provided to each of the plurality of remote users. At 505, annotations for the one or more image are received from each of the plurality of remote users. The annotations and the plurality of medical images are stored together.

Figure 6:
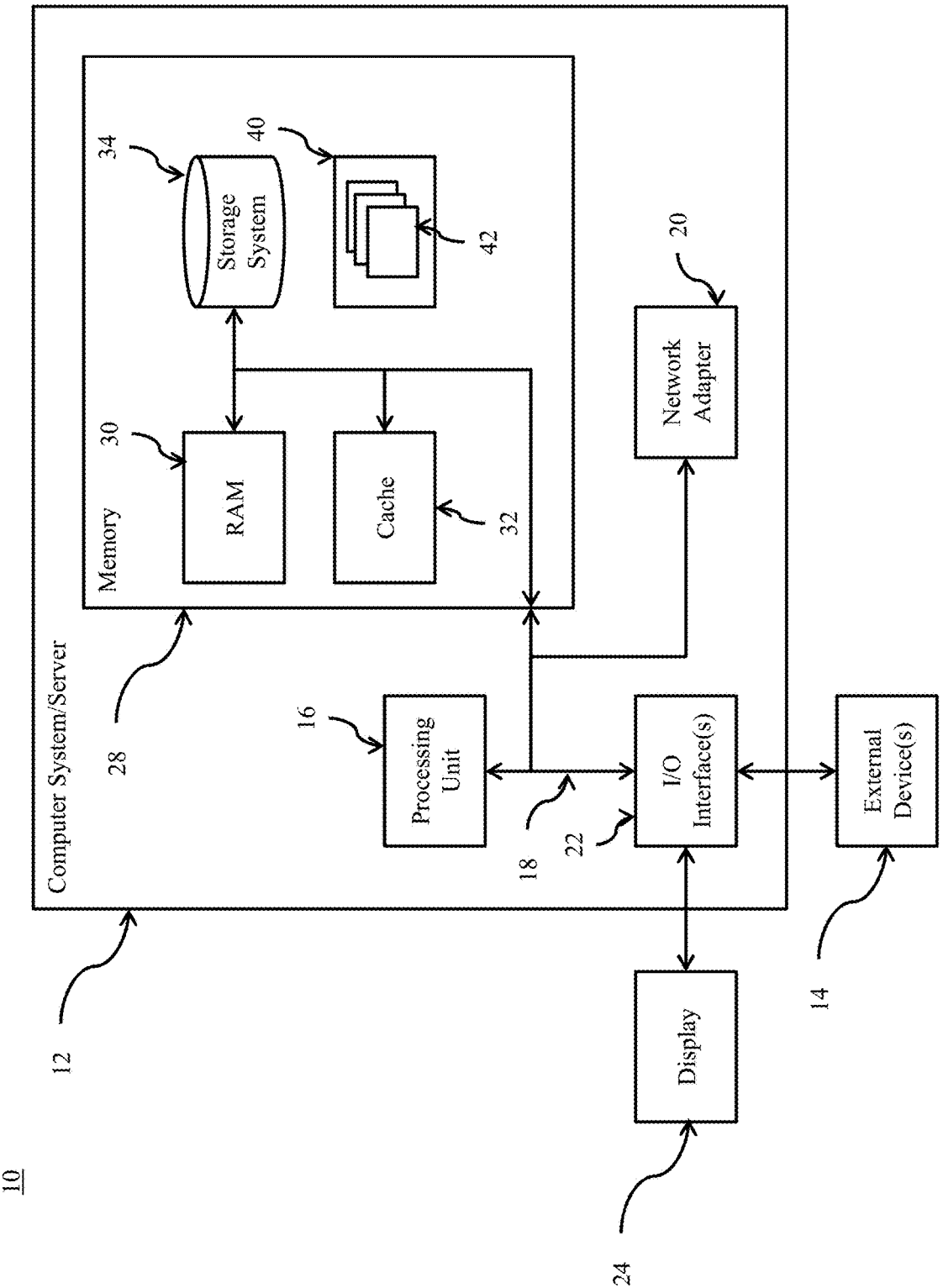
FIG. 6 depicts a computing node according to an embodiment of the present invention.

Referring now to FIG. 6, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 7:
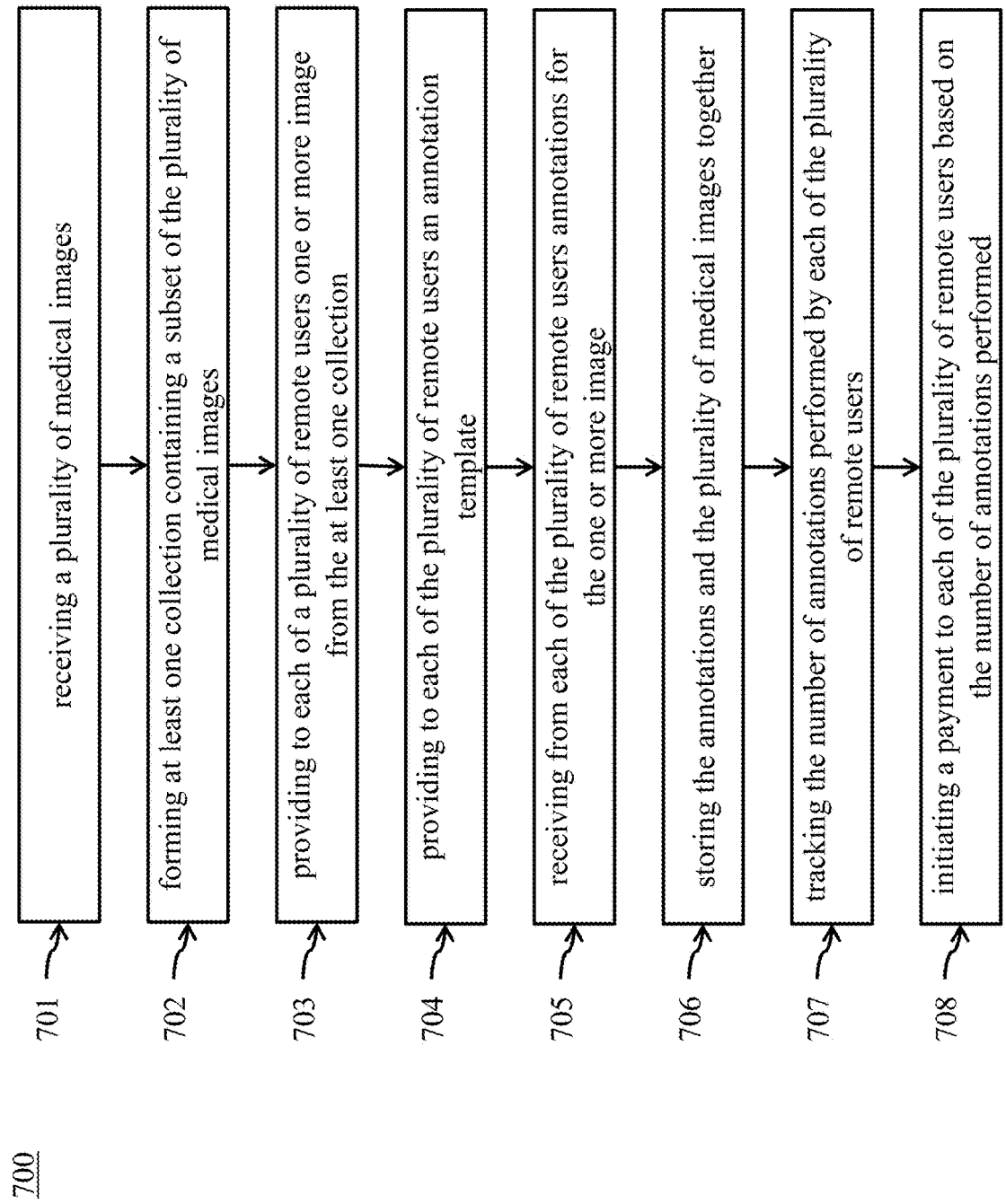
FIG. 7 illustrates a method of annotation of large image datasets according to various embodiments of the present disclosure.

FIG. 7 illustrates a method 700 of annotation of large image datasets. At 701, the method includes receiving a plurality of medical images. At 702, the method includes forming at least one collection containing a subset of the plurality of medical images. At 703, the method includes providing to each of a plurality of remote users one or more image from the at least one collection. At 704, the method includes providing to each of the plurality of remote users an annotation template. At 705, the method includes receiving from each of the plurality of remote users annotations for the one or more image. At 706, the method includes storing the annotations and the plurality of medical images together. At 707, the method includes tracking the number of annotations performed by each of the plurality of remote users. At 708, the method includes initiating a payment to each of the plurality of remote users based on the number of annotations performed.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer program product for annotation of large image datasets, the computer program product comprising a computer readable storage medium having program instructions embodied therewith, the program instructions executable by a processor to cause the processor to perform a method comprising:

receiving a plurality of medical images comprising continuous wave Doppler ultrasound images;

forming at least one collection containing a subset of the plurality of medical images;

providing to each of a plurality of remote users one or more image from the at least one collection;

providing to each of the plurality of remote users an annotation template, wherein the annotation template comprises a selection of a plurality of key points and a contour on each of the one or more image, wherein the key points comprise at least one peak, wherein the annotation template is selected based on an attribute of the one or more image, wherein the attribute comprises a disease label;

receiving from each of the plurality of remote users annotations for the one or more image, wherein receiving annotations comprises obtaining multiple annotations for the same attribute by different annotators by:

receiving first annotations having a first plurality of selected key points from a first of the plurality of remote users for the one or more image according to the annotation template;

receiving second annotations having a second plurality of selected key points from a second of the plurality of remote users for the one or more image according to the annotation template;

determining first measurements comprising a first maximum velocity and a first mean pressure gradient from the first plurality of selected key points and second measurements comprising a second maximum velocity and a second mean pressure gradient from the second plurality of selected key points;

cross-validating the first annotations with the second annotations by comparing the first measurements and the second measurements;

storing the annotations, the first measurements, the second measurements, and the plurality of medical images together.

2. The computer program product of claim 1, wherein the plurality of medical images is received from a picture archiving and communication system.

3. The computer program product of claim 1, wherein the collection is formed from the results of a search of the plurality of medical images.

4. The computer program product of claim 1, wherein the annotation template is selected based on an attribute of the subject of the plurality of the one or more image.

5. The computer program product of claim 4, wherein the attribute comprises age, sex, location, or demographic data.

6. The computer program product of claim 1, wherein each image of from the at least one collection is provided to at least two of the plurality of remote users.

7. The computer program product of claim 6, wherein annotations received for each image from the at least one collection are reconciled.

8. The computer program product of claim 1, wherein the annotations comprise at least one disease label.

9. The computer program product of claim 1, wherein the annotations comprise at least one measurement.

10. The computer program product of claim 1, wherein the annotation comprises at least one contour.

11. The computer program product of claim 1, wherein the annotation comprises at least one segmentation.

12. The computer program product of claim 1, wherein the number of annotations performed by each of the plurality of remote users is tracked.

13. The computer program product of claim 12, wherein a payment to each of the plurality of remote users is initiated based on the number of annotations performed.

14. The computer program product of claim 1, wherein providing the one or more image to each of a plurality of remote users comprises:
   a determination of an access permission of each of the plurality of remote users; and
   a determination of an area of expertise of each of the plurality of remote users.

15. The computer program product of claim 1, wherein forming the at least one collection comprises:
   an association of the subset of the plurality of medical images with metadata for each of the images therein, with a task list, and with a list comprising the plurality of remote users.

16. The computer program product of claim 15, wherein the task list comprises a plurality of desired annotations.

17. The computer program product of claim 1, wherein the annotation template comprises:
   a definition of an annotation task type, and
   a definition of a plurality of tools sufficient to perform the annotation task type; and
   a display of the plurality of tools in a graphical user interface with the one or more image.

\* \* \* \* \*